(12) United States Patent
Didrick (10) Patent No.: US 6,908,489 B2
(45) Date of Patent: Jun. 21, 2005

(54) ARTICULATED ARTIFICIAL FINGER ASSEMBLY

(76) Inventor: Daniel Dean Didrick, 853 Vanderbilt Beach Rd. 259, Naples, FL (US) 34108

(*) Notice: Subject to any disclaimer, the term of this patent is extended or adjusted under 35 U.S.C. 154(b) by 31 days.

(21) Appl. No.: 10/645,211

(22) Filed: Aug. 21, 2003

(65) Prior Publication Data

US 2005/0043822 A1 Feb. 24, 2005

(51) Int. Cl.⁷ .............................................. A61F 2/54
(52) U.S. Cl. ..................................................... 623/64
(58) Field of Search ........................ 623/63, 64; 294/25

(56) References Cited

U.S. PATENT DOCUMENTS

| | | | |
|---|---|---|---|
| 319,776 A * | 6/1885 | Bashore | 623/64 |
| 5,062,855 A * | 11/1991 | Rincoe | 623/24 |
| 5,941,914 A * | 8/1999 | Jacobsen et al. | 623/64 |

* cited by examiner

*Primary Examiner*—Bruce E. Snow
(74) *Attorney, Agent, or Firm*—Raymond Wagenknecht; David R. Preston & Associates (57) ABSTRACT

Disclosed is an articulated artificial finger assembly, which can be controlled by the remaining portion of an amputated finger. An adjacent finger is used to manipulate the device when no finger is present. When the stump or adjacent finger begins to bend at the first knuckle, the rest of the device will react to the movements and articulate in the natural manner of a human finger. There are two embodiments shown which, can accommodate a variety of cases. The first embodiment relates to an amputated finger with a portion of the finger remaining. The second is used when a total finger is absent. In either case, the first embodiment uses a ring that is placed over the remaining stub of the finger and the second embodiment a ring is placed over an adjacent finger. The ring, in either embodiment, actuates upper and or lower actuation drives, which are reciprocally and transversely attached to a pivoting block. The pivoting block is fastened to an adjustable middle phalangeal section. The transversely connected upper and lower actuation drives cause the middle phalangeal section to curl under when articulated. The middle phalangeal section is comprised of two main body parts. The first is an outer phalangeal section and the second phalangeal section is placed inside the outer phalangeal section and fastened thereto. A forward fingertip section is pivotally fastened to a forward end of the inner phalangeal section. A forward end of the upper actuating drive is pivotally connected to the forward fingertip section. A supple cover is placed over the device once it is assembled. An inner supple cover is inserted into the device and sealed along the edges of the outer supple cover. To complete the device a screw is inserted into the fingertip, passing through the supple cover and is then hidden by an artificial fingernail placed thereon.

14 Claims, 8 Drawing Sheets

ARTICULATED ARTIFICIAL FINGER ASSEMBLY

CROSS REFERENCE TO RELATED APPLICATIONS (none)

STATEMENT REGARDING FEDERALLY SPONSORED R & D (none)

FIELD OF THE INVENTION

This invention pertains to an artificial finger assembly, allowing an amputee to regain control of the flexion and extension movements of an artificial finger. The invention accommodates a variety of finger amputation cases from partial finger loss to entire finger loss. When a portion of the finger is present, the partial fingers movement will articulate the invention to follow the natural bending pattern of a finger. When a finger is entirely missing, the movement of an adjacent finger will control the articulation of the invention.

BACKGROUND OF THE INVENTION

Presently the inner construction of an artificial finger is composed of a sponge-like filling. Occasionally, artificial fingers are created with fixable joints as used in action-figure leg joints. These joints provide for stationary positioning of the finger. Presently, technology with smart materials keep many waiting for a new wave of prosthetic advancements. The problems faced with creating electronic artificial fingers for finger amputees are size and cost. Unfortunately, cost will prevent many in need from obtaining expensive electronic prostheses. Creating self-contained electronic finger prostheses offer additional difficulties due to the limited space provided.

Anaplastologists and prosthetists typically create non-articulated silicone finger prostheses for amputee or trauma patients. Finger prostheses commonly are designed for aesthetics more than function and therefore considered somewhat useless in terms of mobility. A finger is created from a mold of the patient's opposing hand, when available, for a near perfect size match. A wax duplicate is created from the mold and bent to mirror the appearance and shape of its original form. The wax finger is cast again and poured up in a durable silicone, creating a silicone duplicate of the missing finger. Silicone fingers are partially filled with a sponge-like material. Enough space is left within the prostheses to snugly fit the patients finger stump. This form of retention is typically sufficient to hold a finger prosthesis, in place. In the prior art, attempts have been made to solve the problem of replacing a missing finger with a mechanical device that was more appropriately designed for a robot than a human.

U.S. Pat. No. 5,941,914 describes an artificial finger device, which can be used to articulate a prostheses. Nearly the entire patent refers to this as a device enabling robots to have a more human appearance as technology advances. There is one line, which states, the most obvious advantage would be for prosthetic devices. This statement is not false, but somewhat misleading. Because it is a finger assembly, the previous statement insinuates it could be used as an artificial finger for finger amputees. This is not true, due to the fact the articulation of the device requires that an articulation bar be retracted from the rear portion of the device. This is the area, which would be butted up against the hand where the device extends. This is when it becomes clear the device could only be used as a finger when an entire hand or arm is missing. This would leave enough space within an artificial hand to permit the device to actuate. This still does not begin to describe the mechanics needed to cause movement of the device, which could easily fill the rest of an artificial hand if not forearm. While the patent described above is of an articulated finger assembly, it offers no benefit to partial or full finger amputations with their hand intact.

DETAILED DESCRIPTION OF THE INVENTION

Figure 1:
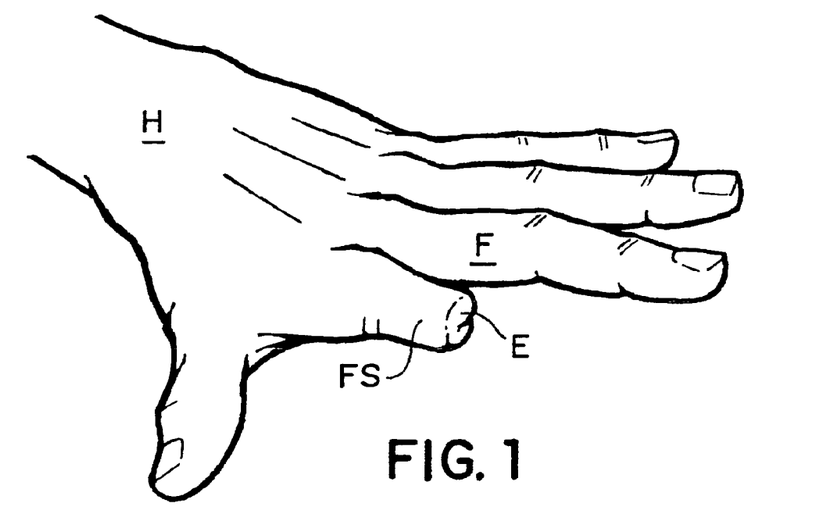
FIG. 1 shows a hand having one finger amputated.

FIG. 1 shows a hand H having a finger, which is partially amputated. The undamaged fingers are indicated as F, while the FS designation indicates a finger stub. The forward end of the finger stub, is shown as E.

Figure 2:
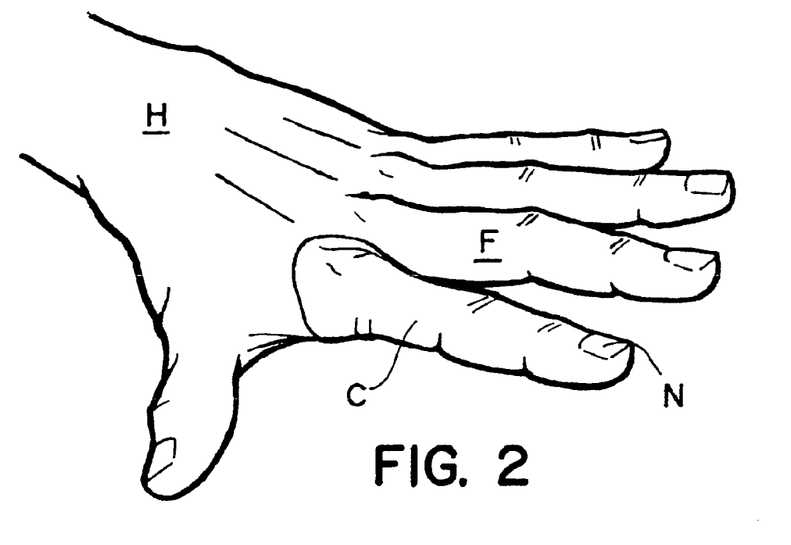
FIG. 2 shows the hand wherein the amputated finger has been replaced.

FIG. 2 shows the hand of FIG. 1, wearing the articulated artificial finger assembly with a C cover thereon, simulating a normal finger. This is how the fully assembled device will appear after having been attached to the hand. An artificial fingernail is labeled as N.

Figures 3, 4, 5:
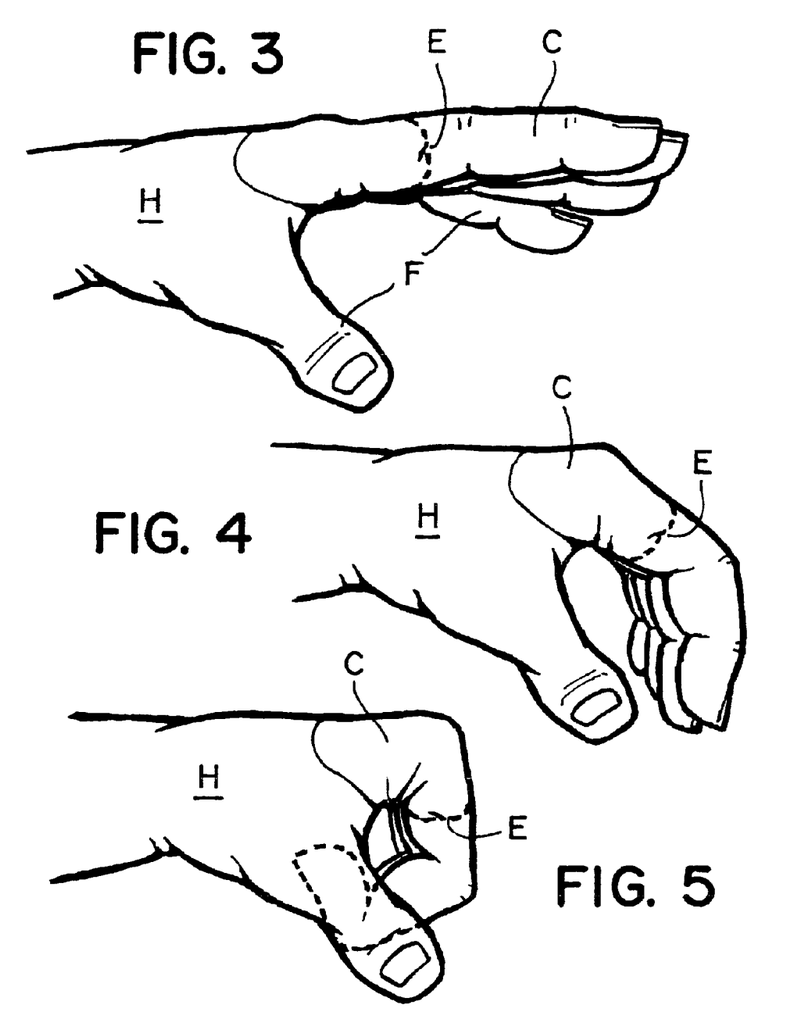
FIGS. 3-5 illustrates a hand while moving the fingers, including the prosthesis.

FIGS. 3-5 illustrate how the artificial finger, with the cover C thereon, participates with the movement of undamaged fingers F. The position of the forward end E of the stub can be seen within the device as it articulates.

Figures 6, 7:
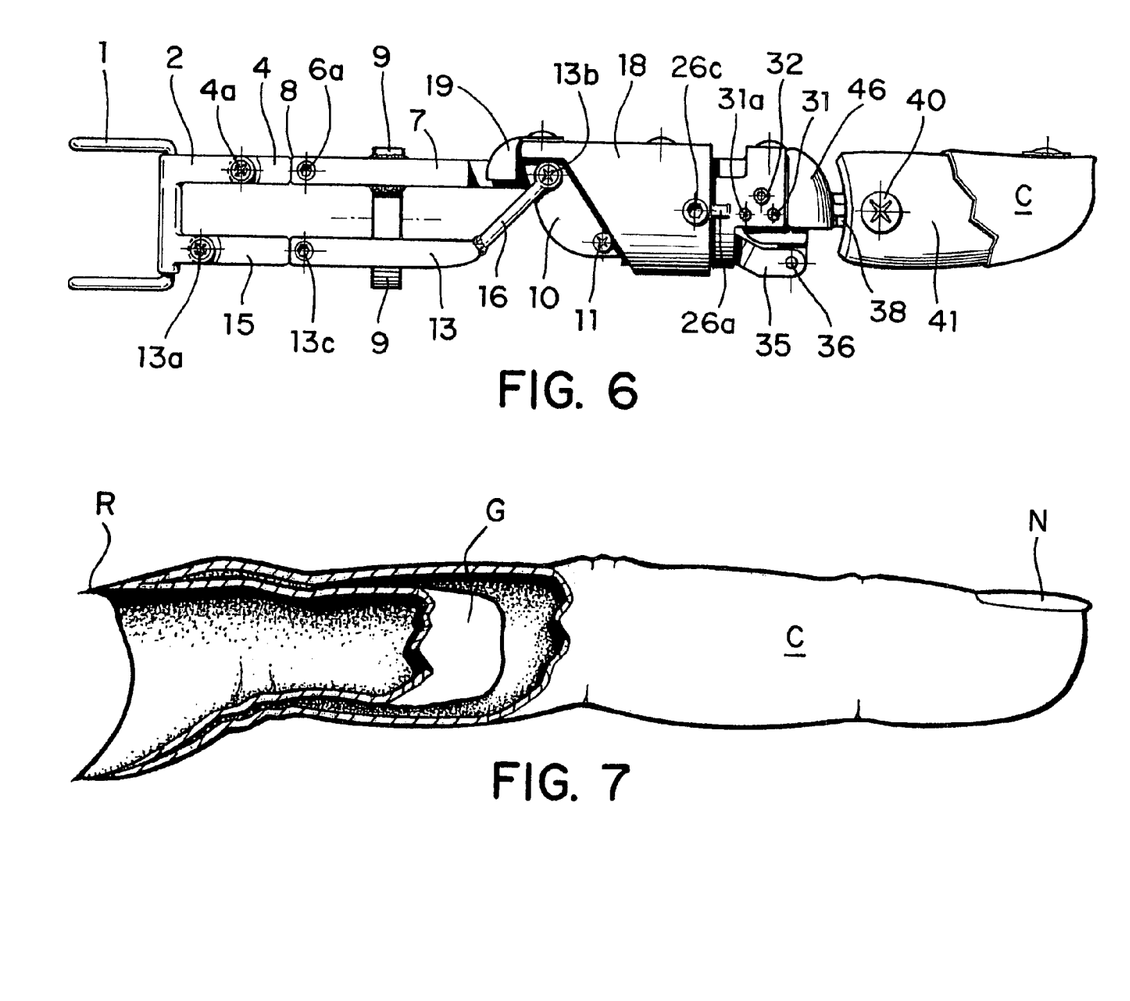
FIG. 6 shows a prosthetic finger fully assembled.
FIG. 7 shows the inner and outer supple cover, which conceals the device.

FIG. 6 shows a fully assembled artificial finger assembly, with a partial cover C showing at the tip. When viewing the cover C in FIG. 7 it becomes evident that the entire mechanical device can be inserted into cover C. The reference characters are fully explained in the isometric and blown up view of FIG. 8. FIG. 6 should be studied in conjunction with FIG. 7 and FIG. 8.

FIG. 7 shows the forward and left side of the inner supple cover G, with the simulated cover C, placed over the inner supple cover G. Please note this is a view of the flexible material, which conceals the entire device once inserted. The inner supple cover G, when completely assembled is inserted through matrix 1 as well as ring 9 of FIG. 6. The outer cover C and inner cover G is sealed together along the outer circumference R, once the device has been inserted.

Figure 8:
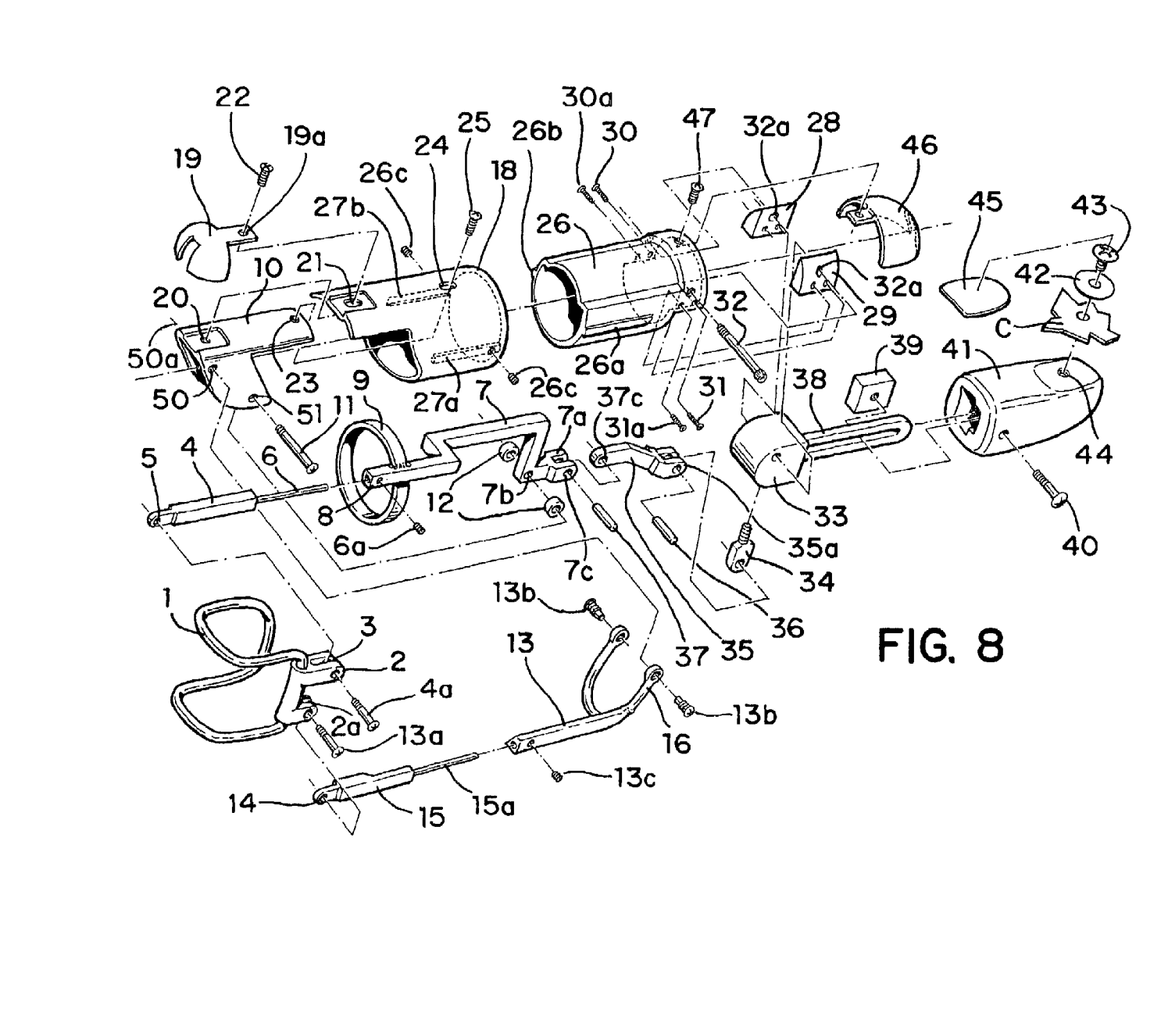
FIG. 8 illustrates an isometric and exploded view of the total prostheses.

FIG. 8 shows the prosthesis in an isometric and blown up illustration. The stationary matrix 1 will slip over the remaining stub of a finger that is to receive this device. The stationary matrix 1 will be slipped over the finger stub FS of FIG. 1, and be stabilized to a knuckle. The forward end of matrix 1 (seen in the direction toward the tip of the finger) has a bracket 2, pivotally attached thereto, which has an upper fork 3 and lower fork 2a. The upper fork 3 will receive eyelet 5 of upper operating drive 4 and will be fastened by way of pivot screw 4a. The upper actuating drive has a length-adjusting rod 6 attached thereto by way of setscrew 6a. Thereby, the length of the prosthesis can be adjusted to proportionally match the length of the remaining fingers. The adjusting rod 6 slides into the upper actuating drive 7 and has a rear end 8 to which finger ring 9 is attached by way of weld or solder. The finger ring 9 slips over the amputated stub once the prostheses is assembled as will be explained further in the application. The forward portion of the upper actuating drive 7 has an eyelet 7b thereon which is to be connected to pivot block 10 by way of a pivot screw 11. Pivot screw 9, will be inserted into eyelet 51, on the pivot block 10, through centering washer 12, eyelet 7b, another centering washer 12, then into a threaded hole on the other side of pivoting block 10, directly across from the opening 51 on pivoting block 10. The above noted elements 1–10 form part of a first section of a first artificial knuckle of the inventive prosthesis. The second part is constructed as follows: Starting again at the stationary matrix 1, the bracket 2 on the matrix 1 has a lower fork 2a, which accepts the eyelet 14 of the rear portion of the lower actuating drive 15 by way of screw 13a. The front end of 15 has a length-adjusting rod 15a attached thereto, which will slide into the rearward end of the lower actuating drive 13. Once adjusted to its proper length, the rear portion of the lower actuating drive 15 and the lower actuating drive 13 are fastened into that position by way of the setscrew 13c. The length adjustment is important so that the prosthesis can be adjusted proportionally to the other fingers. The forward end of the lower actuating drive has a stirrup 16 attached thereto. The stirrup pin pivoting screws 13b fasten the lower actuating drive 13 to the pivot block 10 by way of eyelet 50 and 50a. The latter elements 1–16 form the elements, which is now attached to the pivot block 10. Both the first set elements 1–7a and the second set of elements 13 through 16 are now fastened to the pivot block 10 completing the first articulating knuckle segment. The pivoting block 10 can now be guided into the outer phalangeal section 18 and will be fastened therein in the following manner. Both the pivot block 10 and the outer phalangeal section 18 have openings 20 and 21 respectively to receive screw 22 therein. Included in this assembly is a rear joint cover 19 having an opening 19a therein. Once assembled, the screw 22 will pass through the openings 19a, 21 and 20. A final screw 25 will be inserted through eyelet 24 of the outer phalangeal section 18 and into the threaded opening 23 of the pivot block 10. This completes the overall assembly of the upper and lower actuating drives and how they connect to the pivot block and outer phalangeal section 18. To continue in the assembly of the artificial prosthesis, the inner phalangeal section 26 is inserted into the partially assembled outer phalangeal section 18 in the following manner. The inner phalangeal section has outer and laterally protruding keyways 26a and 26b, which match the inner keyways 27a and 27b, of the outer phalangeal section 18. Once the inner section 26 is inserted into the outer section 18 and aligned by the keys 26 and keyways 27, and the proper distance has been determined, the setscrews 26c will fasten the two sections 18 and 26 together. The forward portion of the upper actuating rod 7 with its fork 7a will now be confined within the pivot block 10, outer phalangeal section 18 and the inner phalangeal section 26. In order to continue an extension of the bar 7 with its fork 7a, link 35 is provided with an opening 37c which is fitted into the fork 7a and fastened therein by way of the pivot pin 37. Link 35 will be made in a variety of lengths to accommodate the length adjustments of the middle phalangeal sections. Attention is now directed to the pivot head 33, which is connected to the fork 35a by way of an eyelet connecting member 34. The pivot head 33, at its forward end, has a length adjusting fork 38 attached thereto. The length adjusting fork 38 serves the purpose of adjusting the length of the final phalangeal section of the device, once finger tip 41 is connected. The pivot head 33 is fastened to the inner phalangeal section 26 by way of a pivotal screw 32. The pivot head has to be centered within the inner phalangeal section by way of centering blocks 28 and 29, which are fastened by way of set screws 30, 30a, 31 and 31a. The forward end of the inner phalangeal section 26 is capped by a forward joint cover 46 and fastened thereto by a setscrew 47. The length adjusting fork 38, once installed, is protruding from the forward end of the phalangeal section 26 and the forward joint cover 46 and passes into and fastens the forward fingertip 40. This is accomplished by a pivot element lock 39 which, when inserted into the forward fingertip 41, will form the forward finger articulation of the inventive prosthesis. Again, the length adjustment fork 38 is designed to allow fingertip 41 freedom to be adjusted before screw 40 is inserted into the fingertip 41 and passes through the length adjusting fork 38 and being fastened in place by tightening the screw into the pivot element lock 39. The forward end of the finger tip articulation will receive an artificial fingernail 45, which will be installed over the cover C, a washer 42 and a set screw 43. As is fully illustrated in FIG. 8 it is now clear that all elements explained above are now contained within the outer phalangeal section 18 and the inner phalangeal section 26. The cover C will cover all of the elements of the inventive prosthesis from the first and second phalangeal sections, beyond the actuating drives 7 and 13 as well as beyond the matrix 1. The joint covers 19 and 46 will round off the middle phalangeal section during articulation to exhibit a continuous flow of the outer cover C.

Figures 9, 10, 11:
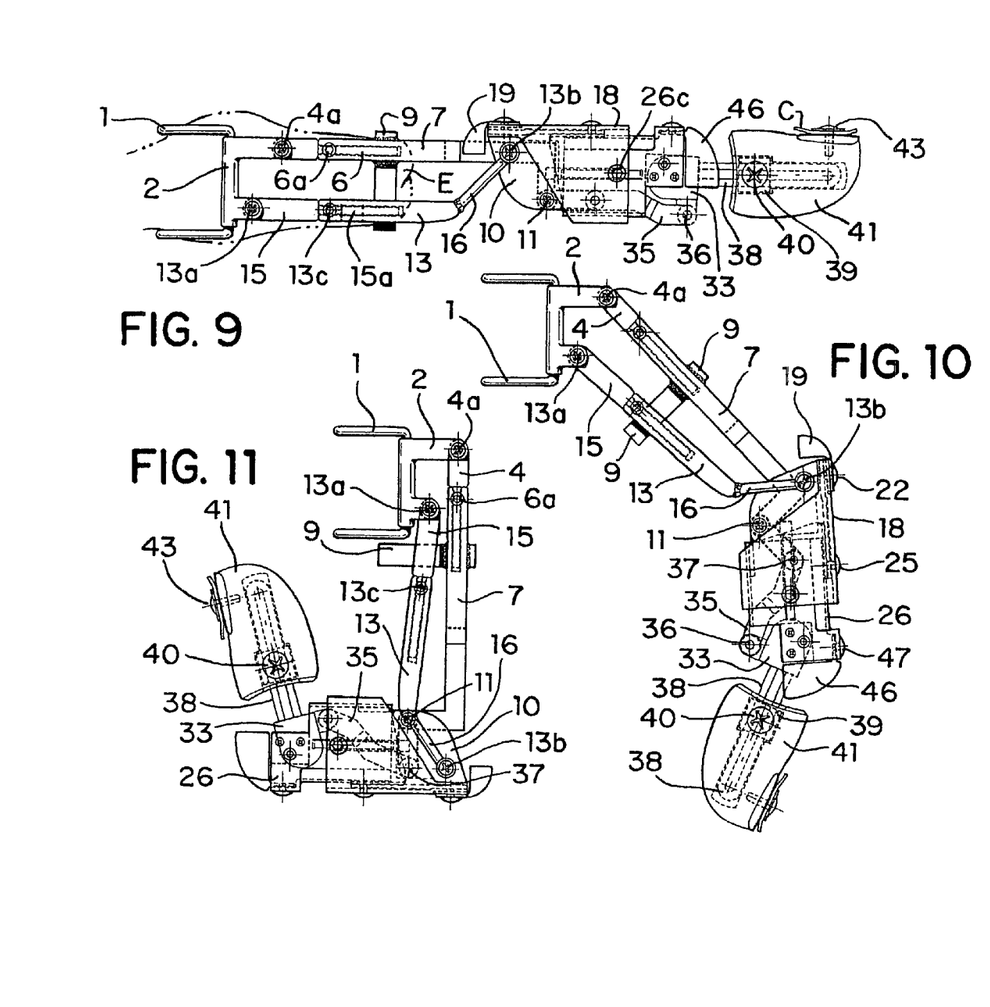
FIGS. 9-11 illustrate the movement of the device from a straight position to completely flexed.

FIGS. 9-11 shows the operation of the flexion and extension movements of the articulated artificial assembly as demonstrated. The device enables someone to control the motion of an articulated artificial finger with leverage gained from the movement of the remaining portion of an amputated finger or stub. When matrix 1 is in place with the stub inserted through matrix 1 and into ring 9 in a straight position, the articulated device is extended in a pointing position shown in FIG. 9. The matrix 1 remains in place while the stub has freedom to move vertically and horizontally. The articulation of the device can most easily be understood by studying the leverage gained from the forward portion of the upper actuating drive 7, which acts as a lever during articulation. When the finger is extended as in FIG. 9, the leverage gained from the upward pressure on the ring 9, holds the middle phalangeal and phalangeal tip in a straight position. FIG. 10 shows a slightly flexed position of the stub along with the assembly. As pressure is applied downward on ring 9, the matrix 1 remains stationary. As the device is pressed down, the screw axis 13b and 11 of the actuating drives, cause the device to curl under. Leverage gained from the movement of fork 7a of the upper actuating drive 7 causes fingertip 41 to articulate by way of link 35.

FIG. 11 shows a fully articulated view, where the middle phalangeal section and phalangeal tip is completely articulated in a flexed position. The device follows the natural bending pattern of a finger controlled by the motion of the stub. The following description is a second embodiment of the invention wherein an entire finger has been amputated.

Figure 12:
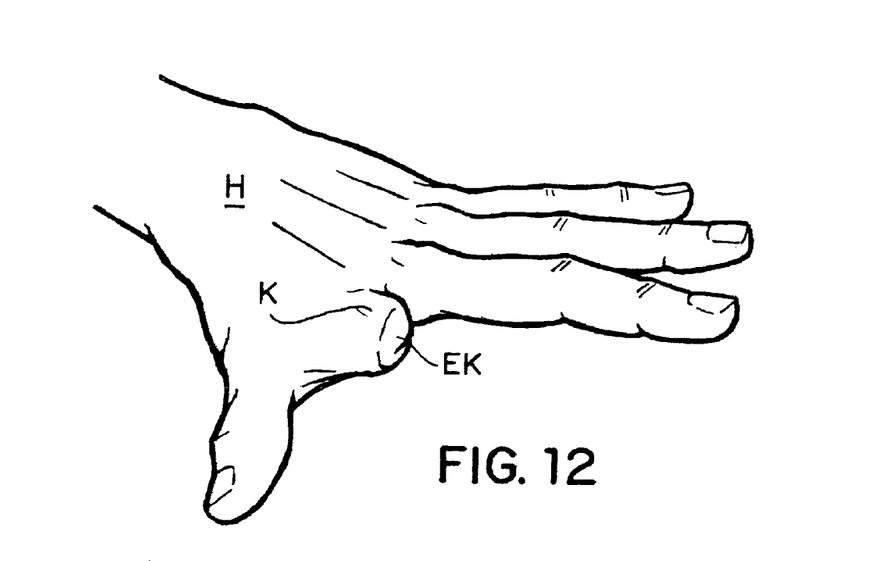
FIG. 12 illustrates a hand with a finger completely missing except the knuckle.
Figure 13:
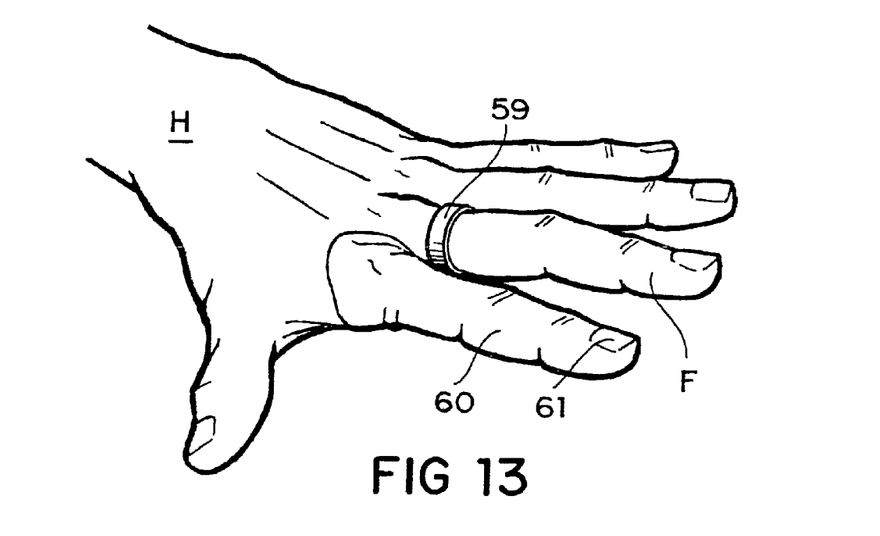
FIG. 13 illustrates a simulated finger after the prosthesis has been attached.

FIG. 12 illustrates the hand H whereon a finger has been completely amputated leaving the end of the knuckle EK only. Obviously the remaining stub of the finger in the embodiment 1 cannot be used to activate the movement of the artificial finger. Therefore the adjacent finger next to the missing finger is being used for this purpose. Consequently, in FIG. 13 there is a ring 59, which makes this connection shown in subsequent Figures. Also, FIG. 13 shows a supple cover 60 shown in previous figs. as C which is placed over the artificial finger after it is installed including a simulated fingernail 61.

Figure 14:
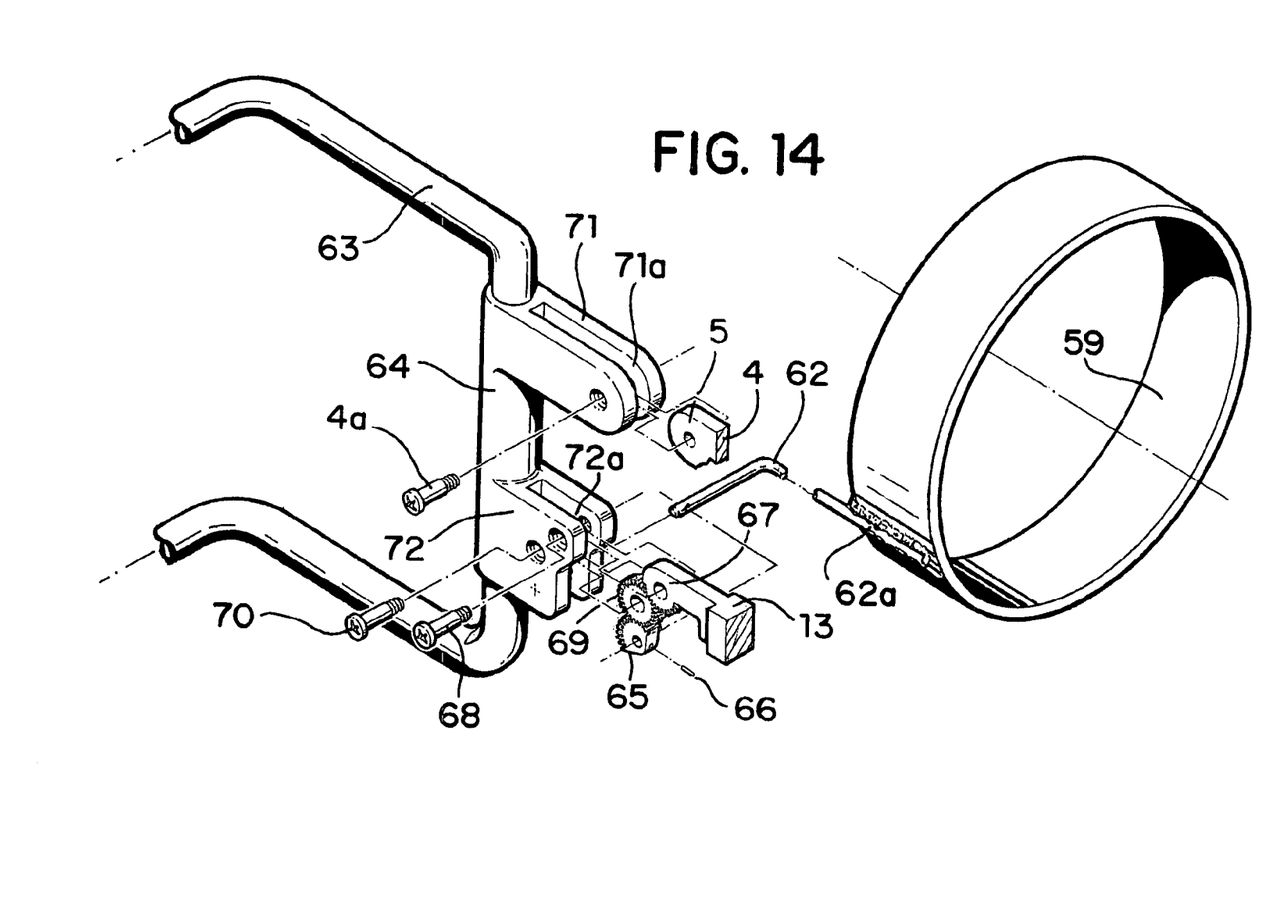
FIG. 14 shows the differences in the second embodiment when operated by an adjacent finger.

FIG. 14 illustrates the connection between the normal finger and the mechanism that activates the artificial finger, which is adjacent to the normal finger. To this end the activating ring 59 on the adjacent finger has an extension wire or rod 62 which is fastened to ring 59 by way of welding or soldering and forms a right angle to be explained below. This second embodiment includes a stationary matrix 63, which is installed over the knuckle of the missing finger, which operates in a similar manner as does the stationary matrix 1 in the first embodiment. The stationary matrix 63 has a bracket 64 attached thereto which has an upper extension 71 being formed into a fork 71a, which will receive therein a rear portion of the upper actuating drive 4, by way of the eyelet 5 and fastened therein by way of the pivot screw 4a. The bracket 64 has a lower and shorter extension 72 thereon which includes a fork 72a. The extension wire 62 being attached to the ring 59 and at a right angle thereto continues to extend into a first and lower segmented gear 65 which is located inside the fork 72a and fastened thereto by way of setscrew 66. There is an upper and segmented gear, which is received in the fork 72a and is held in place therein by way of pivot screw 68. A driving connection is made between the upper segmented gear 67 and the lower segmented gear 65 threw the interposition of an intermediate gear 69, which is pivotally mounted in the fork 72a by way of a pivot screw 70. The upper segmented gear 67, is an extension of the rear portion of the lower actuating drive 15 which forms the basis of the first embodiment as well as the rear portion of the upper actuating drive 4. From here on in, the elements of the second embodiment operate in the same manner as was explained in the first embodiment. From all of the above, it is now clear how the artificial and articulated finger is operated by either a remaining stub of an amputated finger or by an adjacent finger. An adjacent finger is used when a finger has been completely amputated, by making only minor operating changes of the device.

Figure 15:
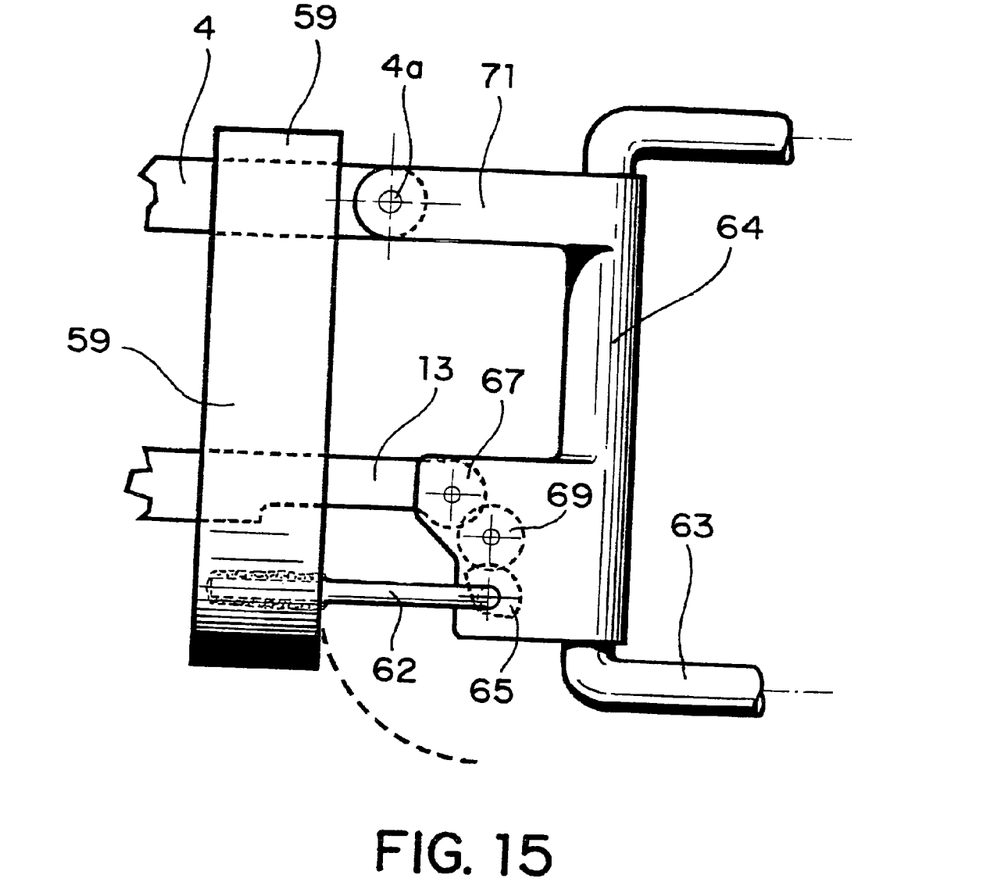
FIG. 15 shows an assembled side view of FIG. 14.

FIG. 15 is a side view of the second embodiment described in FIG. 14. It is now clear how the ring 59 connects to the extension wire 62 and inserts into the lower segmented gear 65. In this embodiment the lower actuating drive actuates the device whereas in the first embodiment the ring controls the upper actuating drive.

What is claimed is:

1. An articulated finger assembly adapted to be operated by a remaining stub of an amputated finger, said artificial finger includes a stationary matrix configured to be placed beyond said remaining stub, a lower actuating drive being pivotally attached to said stationary matrix and an upper actuating drive being pivotally attached to said stationary matrix, said upper and lower drives are reciprocally and transversely interconnected to a pivoting block, in a pivoting fashion, said upper and lower drives compatibly configured with said remaining stub, thereby and forming a first articulating knuckle segment.

2. The artificial finger of claim 1, wherein an outer phalangeal section is fastened to said pivoting block.

3. The artificial finger of claim 2, further comprising a connecting rod to pivotally connect said actuating drive to a pivot head.

4. The artificial finger of claim 3, wherein said pivot head has an extension attached thereon, said extension with means to fasten a fingertip phalangeal segment thereto.

5. The artificial finger of claim 4, wherein the said extension is fastened to said pivot head with means for adjusting the relative position between said pivot head and said fingertip element.

6. The artificial finger of claim 2, wherein said outer phalangeal section receives an inner phalangeal section having a rear and forward end, said pivot head is pivotally fastened to said forward end of said inner phalangeal section, thereby forming the second and articulating section of said artificial finger.

7. The artificial finger of claim 6, wherein said forward end of said inner phalangeal section has a joint cover fastened thereon.

8. The artificial finger of claim 7, wherein both said outer and inner phalangeal sections are fastened relative to each other including means for adjusting a relative position to each other.

9. The artificial finger of claim 2, wherein a rear end of said outer phalangeal section has a joint cover fastened thereon.

10. The artificial finger of claim 1, wherein both said upper and lower actuating drives have means for adjusting their lengths thereof.

11. The artificial finger of claim 1, including a means to fasten said upper and or lower articulation drives to the said remaining stub of an amputated finger.

12. The artificial finger of claim 11, wherein a means to fasten said upper and or lower articulation drives is fastened to an adjacent finger when no remaining finger stub is available, including means for rotating said lower actuating drive, and an inner supple cover is inserted through the said matrix and sealed to the said outer supple cover.

13. The artificial finger of claim 1, including a supple cover placed over said artificial finger once assembled.

14. The artificial finger of claim 13, wherein an inner supple cover is inserted through the said matrix and sealed to the said outer supple cover.

* * * * *